United States Patent [19]
Vineberg

[11] Patent Number: 5,928,797
[45] Date of Patent: Jul. 27, 1999

[54] TEMPORARY TATTOO DEVICE AND METHOD

[75] Inventor: Scott Vineberg, Montreal, Canada

[73] Assignee: Deliquescence Holdings, Inc., Montreat, Canada

[21] Appl. No.: 08/924,961

[22] Filed: Sep. 8, 1997

[51] Int. Cl.⁶ .............................. B32B 27/00; B41M 3/12
[52] U.S. Cl. ........................ 428/500; 428/42; 428/914
[58] Field of Search .............................. 424/402; 428/40, 428/43

[56] References Cited

U.S. PATENT DOCUMENTS

| | | | |
|---|---|---|---|
| 4,515,773 | 5/1985 | Herlihy | 424/59 |
| 4,522,864 | 6/1985 | Humason et al. | |
| 4,594,276 | 6/1986 | Relyea | 428/40 |
| 4,665,912 | 5/1987 | Burton | 128/303 R |
| 5,015,263 | 5/1991 | Albrecht | 8/680 |
| 5,052,418 | 10/1991 | Miller | 132/319 |
| 5,302,224 | 4/1994 | Jenkins | 156/230 |
| 5,421,765 | 6/1995 | Lehmann | 446/296 |
| 5,470,351 | 11/1995 | Ross et al. | 607/95 |
| 5,578,353 | 11/1996 | Drew | 428/43 |
| 5,601,859 | 2/1997 | Penaluna | 426/5 |
| 5,776,586 | 7/1998 | Lipper | |

FOREIGN PATENT DOCUMENTS 2 273 266  6/1994  United Kingdom .

*Primary Examiner*—Thurman K. Page
*Assistant Examiner*—Sharon Howard
*Attorney, Agent, or Firm*—Litman, Kraai and Brown, L.L.C.

[57] ABSTRACT

The invention concerns a device and method for applying temporary tattoos. The device is a pocket enclosing a dye. The outer layers of the pocket are impermeable to the dye. The pocket has a removable bottom layer. When the bottom layer is removed, the now exposed inner layer of the pocket, which has dye-permeable and dye-impermeable portions, is adhered to an appropriate location of a user's skin. The user's skin is then exposed to the dye and a tattoo will form in a pattern corresponding to portions of the inner layer (or layers) permeable to the dye. Using the method, a user may cut out and remove a pattern from a dye-impermeable layer of material. The layer is adhered to an appropriate location of a user's skin. The user applies the dye over the layer. The user then securely adheres a dye-impermeable backing layer to the layer of material, thereby preventing leakage of the dye between the layer of material and the backing layer.

31 Claims, 3 Drawing Sheets

TEMPORARY TATTOO DEVICE AND METHOD

FIELD OF THE INVENTION

The invention relates to tattoos and in particular to a method and apparatus for applying temporary tattoos.

BACKGROUND OF THE INVENTION

Various methods of dying or tattooing the skin have been used for centuries. Simply painting the skin, for example, requires ideally a certain degree of artistic ability and an understanding of various paints or dyes and their effect on skin. Tattooing, historically, has typically involved a tattoo artist dying the skin, through a painful process using needles and permanent dyes. Permanent tattoos are often seen as undesirable due to their permanent nature, their cost, the pain involved, the possible health risks associated with contaminated needles and the need for a skilled tattoo artist. Although some people are willing to obtain a permanent tattoo, they often would like to experience the same tattoo in the same location and size on a temporary, trial basis first.

Other people who would never consider obtaining permanent tattoos would obtain temporary tattoos if the temporary tattoo were safe and easy to apply, required no artistic skill or knowledge of dyes or paints and if the user could control the duration of the tattoo on the skin. Such temporary tattoos would be especially desirable for those who may want a temporary tattoo for a special occasion, for example, or for the duration of a holiday.

There are several existing methods and devices for applying temporary tattoos. For example, U.S. Pat. Nos. 5,578,353 and 5,601,859, which were issued to Drew in 1996 and Penaluna in 1997, respectively, describe temporary tattoos which can be transferred from a substrate to the recipient's skin by wetting the substrate and applying the substrate to the skin. Such forms of temporary tattoos typically either create superficial markings on the skin or else involve the transfer of a coloured thin film to the skin, both which tend to wash off or fade shortly after being applied. As well, the user typically cannot control the length of time the temporary tattoo will remain on the skin. Further, due to the process involved in creating the substrate, it is unlikely that a user would or could create his or her own tattoo designs.

Several methods are known for applying temporary tattoos using the dye henna. One method involves the use of henna paste applied with a vessel similar to a pastry bag used to apply cake icing. The dye is carefully applied to the user's skin in the desired pattern. This method requires artistic skill, and patience by the artist and the user while the dye is being applied. This method also requires the user to remain still for hours while the dye sets and the henna must be repeatedly moistened to prevent the dye from drying or flaking.

Henna can also be processed into a drier paste form (similar to plasticene) where strips of henna may be carefully pressed onto the user's skin in a desired pattern. This method also requires artistic skill, patience and stillness by the user while the dye dries.

If henna is used in a liquid form, a stencil with a pattern removed therefrom may be applied to the user's skin onto which the henna may be poured to form a temporary tattoo in the shape of the pattern. However, the henna must be repeatedly re-hydrated during the process to avoid premature drying and cracking of the henna. Also, the user must be very careful to remain still during application and drying of the dye to avoid leakage or spillage of the dye beyond the pattern.

Because of the need to use two hands to apply henna according to these known methods, and because artistic skill is typically required, one is unlikely to be able to apply such temporary tattoos by oneself. Further, because of the skill and time required to apply these tattoos, the cost is often high. These methods also do not lend themselves to the mass production of temporary tattoos.

There are also several methods known for creating temporary suntan "tattoos". For example, U.S. Pat. No. 5,470,351, which was issued to Ross in 1995, describes a method for creating a suntan "tattoo" where a piece of material, which is capable of blocking the tanning rays from the sun, is adhered to a user's skin. When the user exposes the skin to sunlight (or other tanning source) the skin will tan except under the material. Accordingly, the pattern defined by the material is "tattooed" onto the skin.

A similar concept is described in U.S. Pat. No. 5,052,418, which was issued to Miller in 1991. This patent describes a piece of material adhered to the skin in which a pattern has been previously cut out and removed from the material. Sun block is then applied to skin in the cut out pattern. The material is then removed from the skin. When the skin is exposed to sunlight, the pattern protected by the sun block will create a temporary "tattoo" because that area will not tan at all or at a rate different from the surrounding skin.

Both of these suntan "tattoo" methods obviously require prolonged sun tanning, which is now frequently avoided due to increased awareness of the risk of skin cancer. Further, these methods require warm sunny weather or access to tanning salons. Obviously, as well, one has no choice of colour for the "tattoo". Such methods may also be problematic when one would like to apply a temporary tattoo to a private area of the body.

SUMMARY OF THE INVENTION

It is an object of the invention to obviate or mitigate one or more of the above identified disadvantages.

According to one broad aspect, the invention provides a dye enclosed within a dye impermeable pocket. A dye-impermeable bottom layer of the pocket is removed and the pocket is adhered to a user's skin. A tattoo is produced on the user's skin as defined by dye-permeable pattern(s) of the pocket through which the dye passes as it exits the pocket. The pocket provides a means for controlling the pattern of the tattoo, the place of exposure on the user's skin, the duration of exposure of the dye to the skin and the duration of the resulting tattoo on the skin. According to another broad aspect, the dye is arranged in a pre-determined pattern within the pocket. After the pocket is adhered to a user's skin, a tattoo is produced on the user's skin as defined by the predetermined pattern of the dye.

According to yet another broad aspect, the invention provides a device for applying a temporary tattoo, the device comprising a pocket containing a dye, the pocket being defined by a removable bottom layer and a backing layer which are impermeable to the dye, the pocket having an inner layer interposed between the dye and the removable layer, the inner layer having a predetermined pattern defined by dye-impermeable and dye-permeable portions.

According to yet another broad aspect, the invention provides a device for applying a temporary tattoo, the device comprising a pocket containing a dye, the pocket being defined by a removable bottom layer and a backing layer which are impermeable to the dye, the dye being interposed between the backing layer and the bottom layer and the dye being in a predetermined pattern.

According to yet another broad aspect, the invention provides a method for applying a temporary tattoo using a dye, the method comprising the following steps: creating a pattern in a layer of material, the pattern being defined by dye-permeable and dye-impermeable portions; securely adhering the layer of material onto a user's skin; applying the dye over the layer of material; securely adhering a dye-impermeable backing layer to the layer of material whereby no dye can leak between the backing layer and the layer of material.

Advantages of the present invention include the provision of relatively inexpensive temporary tattoos which: allows the user to determine the duration of the tattoo on the skin (from a few days to a few months, for example); helps to avoid the spilling or accidental staining of the dye; helps to avoid the likelihood of the dye inadvertently evaporating, dehydrating, cracking or flaking due to exposure to air; allows the user to apply a temporary tattoo that is not merely superficial but that penetrates the skin, if desired; allows the user to test a tattoo on a temporary basis prior to obtaining a permanent tattoo; allows a tattoo artist to lay a temporary tattoo on a client's skin in the form of a desired permanent tattoo, which may be useful especially where the creation of the permanent tattoo requires several sittings; allows for the controlled application of a temporary tattoo; avoids the pain and permanence of permanent tattoos; allows medical workers to temporarily mark an area of a patient's skin for a subsequent medical procedure; provides the user with the ability to create his or her own tattoo design without training or artistic skill using, if desired, traditional and natural dying agents such as henna or indigo, for example.

BRIEF DESCRIPTION OF THE DRAWINGS

Preferred embodiments of the invention will now be described with reference to the attached drawings in which:

FIG. 4b is a cross-sectional view of the combination of an inner layer, an adhesive layer and a removable layer, taken along line b—b of FIG. 4a;

DETAILED DESCRIPTION OF THE PREFERRED EMBODIMENTS

Figure 1A:
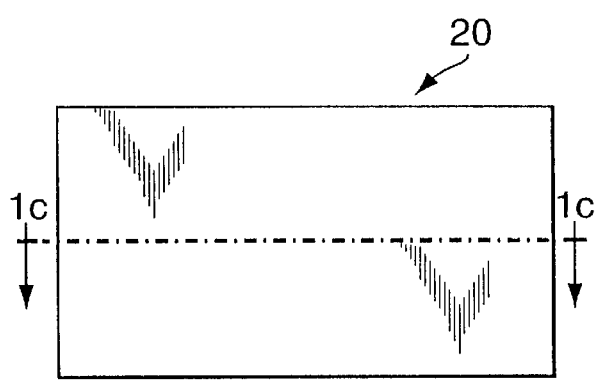
FIG. 1a is a top view of a tattoo pocket, showing a backing layer, in accordance with an embodiment of the present invention.

Referring to FIG. 1a, there is illustrated a cross-sectional view of a device for applying a temporary tattoo in accordance with an embodiment of the present invention. The device may be conveniently referred to as a pocket or tattoo pocket, and is generally designated 20.

Figure 1B:
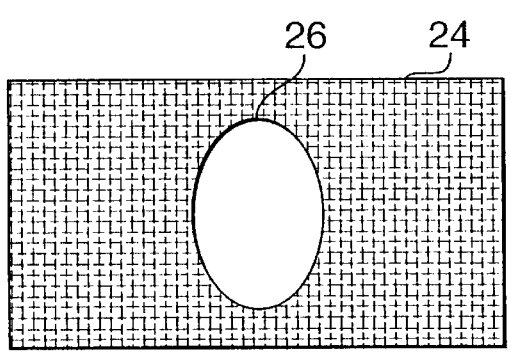
FIG. 1b is a top view of an inner layer, with a pattern removed therefrom.
Figure 1C:
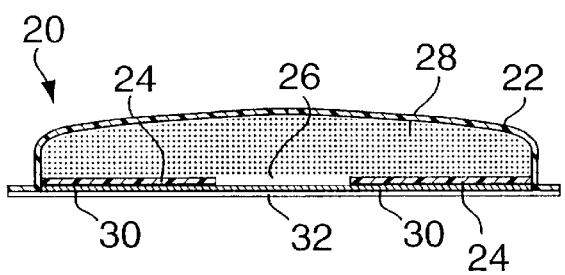
FIG. 1c is a cross-sectional view of the tattoo pocket taken along line c—c of FIG. 1.

In the simple embodiment shown in FIGS. 1a–1c, which may be referred to as a stencil version of the tattoo pocket, the tattoo pocket 20, which is a self-contained unit, consists of several layers of material and one layer of a dye 28, as shown in FIG. 1c. The outer layers 22, 32 of the pocket 20 are formed of material impermeable to the enclosed dye 28.

The backing layer 22, as shown in FIGS. 1a and 1c, in top and cross-sectional views, respectively, forms the back and sides of the pocket 20. The dye or dye layer 28 is below the backing layer 22. An inner layer (or stencil layer) 24 is below the dye layer 22. As shown in FIG. 1b, a top view of the inner layer 24, the pattern 26 to be tattooed on a user's skin has been cut out and removed from the inner layer 24. As will be described in further detail below, the inner layer 24 can be made up of one or more layers. Further, the pattern 26 defining the tattoo need not necessarily be a hole within inner layer 24. For example, pattern 26 could be a dye-permeable material whereas the remainder of inner layer 24 is formed of dye-impermeable material. In other words, the tattoo is defined by dye-impermeable and dye-permeable portions of the inner layer, as described in greater detail below.

The edges of the inner layer 24 adjacent the backing layer 22 are preferably adhered to the backing layer 22 at the sides of the pocket to prevent leakage or flow of the dye 28 anywhere but through pattern 26.

On the under surface of inner layer 24 is an adhesive or adhesive layer 30. The adhesive 30 adheres the inner layer 24 to a removable or peel-away layer 32. As mentioned above, the pocket 20, as shown in FIG. 1c, is a self-contained unit, which prevents the enclosed dye 28 from drying out or leaking from the pocket 20.

To use the pocket 20, the user decides upon an appropriate location of the body to tattoo. The user then peels away the peel-away layer 32 from the inner layer 24 (the peel-away layer 32 and the inner layer 24 are separably adhered by adhesive 30). In the preferred embodiment, the inner layer 24 is then adhered to the appropriate location of the user's body by adhesive 30. The dye 28 then seeps onto the user's skin in the form of pattern 26.

In the preferred embodiment, the dye 28 is of a type which penetrates the user's skin. In general, depending upon the type of dye 28 used and the volume initially contained within the pocket 20, the longer the pocket 20 is adhered to the user's skin, the longer the resulting tattoo will remain on the skin before it fades completely. When the pocket 20 has remained on the user's skin for an appropriate period of time, the user removes the pocket 20 from the skin (that is, the adhesive 30 separably adheres the inner layer 24 of the pocket to the user's skin). Of course, if there is any dye 28 remaining in the pocket 20 when the pocket is removed from the skin, the user must be careful to avoid spillage or leakage of the dye 28 onto the skin outside of the area of skin just tattooed.

The pocket 20 can conceivably be of any desired dimensions. However, the larger the dimensions, the more unwieldy the application of the tattoo pocket 20 to the user's skin may become.

With respect to types of materials for the various layers, the possibilities are virtually unlimited. Several possibilities are considered below for example purposes only.

The backing layer 22 and the peel-away layer 32 must be impermeable to the dye 28. Preferably, the backing layer 22 will be sufficiently durable so as not to puncture if scratched, scraped or accidentally hit while being worn by the user. Suitable materials include various types of rubber, plastics, polyesters or nylons.

The inner layer 24, or portions of inner layer 24, must be impermeable to the dye, in order to define a desired pattern. In the preferred embodiment, the inner layer 24 is a hypo-allergenic material which can be smoothly applied over the desired area of the user's skin and which is sufficiently flexible and strong enough to maintain the pattern 26 whether applied to a relatively flat and smooth part of the body, such as the user's back, or whether applied to a curved part of the body, such as the user's arm or shoulder. The preferred materials minimize bleeding or spreading of the dye beyond the perimeter of the tattoo pattern 26. It is believed that a suitable material for the inner layer is a thin (perhaps 0.03 mm thick) polyethylene film such as would be available from 3M Health Care (of St. Paul, Minn.). It is also believed that other types of plastic, woven fabrics and rubber could be used, for example.

According to one embodiment, before the pocket 20 is assembled, the pattern to be tattooed is cut in the inner layer 24 and the material within the pattern is removed, thereby leaving an opening 26 within inner layer 24 defining the pattern. The pattern may be cut by a computer-controlled cutter or by dye-cutting, for example.

The adhesive 30 is hypo-allergenic, pressure-sensitive and is preferably water resistant and adheres well to the user's skin. In the preferred embodiment, the adhesive 30 allows for the adhesion of the inner layer 24 to the peel-away layer 32; and when the peel-away layer 32 has been removed (ie: peeled away) the adhesive 30 is able to adhere the inner layer 24 securely to the user's skin.

The peel-away layer 32 can be any material that is impermeable to the dye 28 and which can be securely adhered to the inner layer 24 by means of adhesive 30. It is believed that a suitable combination of the inner layer 24, adhesive 30 and peel-away layer 32 is available from 3M Health Care (of St. Paul, Minn.).

The dye 28 is preferably one which is non-toxic; can penetrate the skin; and which will remain on the skin, as a tattoo before fading completely, in direct proportion to the length of time the pocket 20 is adhered to the skin. Of course, one could, if desired, also use a dye which does not significantly penetrate the skin.

In the preferred embodiment, the time required for the dye to penetrate the skin can be reduced by heating the dye. For example, a hot compress can be applied over the tattoo pocket 20 while the pocket is adhered to the user's skin to accelerate penetration of the dye into the skin (and thereby reduce the amount of time the pocket 20 must be worn by the user to obtain a tattoo that will remain on the user's skin for a given amount of time). Appropriate types of dye include henna or indigo, for example.

As noted above, an infinite number of other types of dye, both naturally occurring and synthetic, may be used. Further, the dye may be in liquid, gel or solid form.

A solid dye may be useful where a long shelf-life is desirable and where it is desirable to have the dye, when it is in the pocket, in the form of the pattern itself, rather than requiring the use of dye-permeable and dye-impermeable portions to define a tattoo pattern.

Figure 1D:
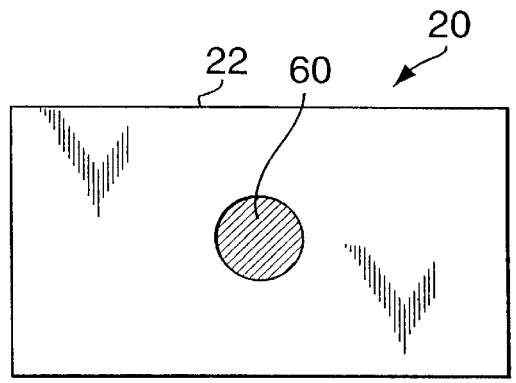
FIG. 1d is a top view of a backing layer having a moisture-permeable portion.

If the dye is in dry or solid form (for example, a powder) then depending upon its characteristics, it will seep onto or into the user's skin after it is combined with heat or moisture which may either be provided by the heat or moisture of the user's skin or by the application of heat or moisture to the pocket 20 from an external source. In the preferred embodiment, the moisture is applied through the backing layer 22. For example, if moisture is applied to the dye in the form of water, then as shown in FIG. 1d, a top view of a backing layer 22, a portion of the backing layer 22 has a water-permeable portion 60, through which an appropriate volume of water can be poured.

Figure 1E:
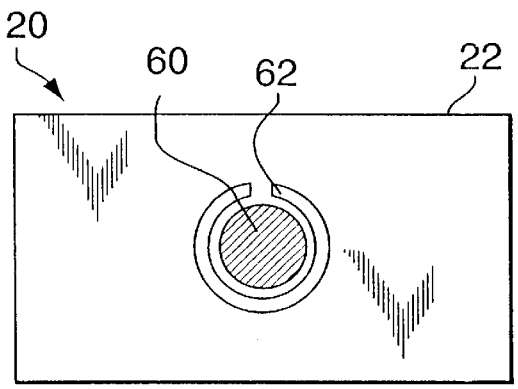
FIG. 1e is a top view of the backing layer of FIG. 1d further comprising a peel away strip surrounding the moisture-permeable portion.
Figure 1F:
FIG. 1f is a top view of a dye-impermeable seal or covering for the moisture-permeable portion of FIG. 1e.

In the preferred embodiment, after the water has been applied to water-permeable portion 60, a dye-impermeable layer (or plug) 64, as shown in the top view in FIG. 1f, is then adhered, by one of any number of methods, to the backing layer 22 over the water permeable portion 60, to prevent leakage of the water. One method for applying the dye-impermeable layer 64 over the backing layer 22 involves the use of a peel-away strip 62 surrounding the perimeter of the water-permeable portion 60, as shown in FIG. 1e. Upon peeling away the peel-away strip 62, a layer of clean adhesive (not shown) is revealed to which the water-impermeable layer 64 may be applied.

When using a dry or solid dye, either the inner surface of the backing layer 22 or a separate layer (not shown) will preferably contain material suitable to absorb the water and which allows the dye to be moistened over time, especially when the dye is unable to completely absorb the water immediately following introduction of the water.

Figure 1G:
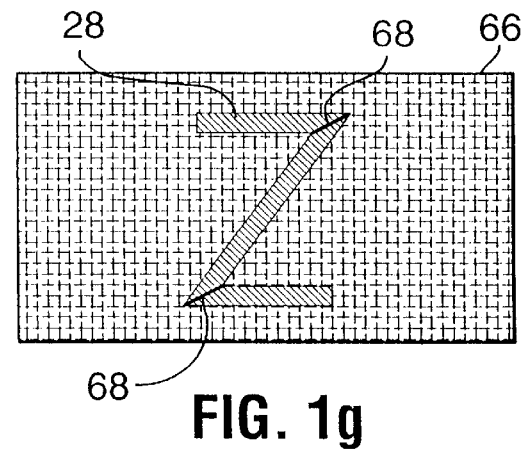
FIG. 1g is a bottom view of a layer of material in which solid or gel dye is adhered, imbedded or partitioned in the form of the letter "Z"

If, upon application of the water, the solid dye becomes a liquid (ie: flows easily), then the various different embodiments of the inner layer as described above and below can be used to define a tattoo. However, if the solid dye is of a type that, once moistened, flows very slowly, or almost not at all, then the dye can, during manufacture of the pocket, either be adhered to or imbedded in or partitioned on a layer of material in the form of the desired tattoo. For example, FIG. 1g shows a bottom view of solid (or gel) dye 28 adhered to, imbedded in or partitioned in a lower surface of material 66 in the form of the letter "Z". In this embodiment, the lower surface of layer 66 could be the inner surface of backing layer 22 or layer 66 could be a separate layer of material, located below backing layer 22. In the simplest form of this embodiment, the backing layer 22 is adhered to the upper surface of layer 66 and a peel-away layer (not shown in FIGS. 1d–1g) is adhered to the lower surface of layer 66. To apply a tattoo, the peel-away layer is peeled away and the lower surface of layer 66 is adhered to the user's skin (in the case of a dye gel, the dye 28 itself may act as an adhesive; or an adhesive may be applied to the lower surface of layer 66 to areas not occupied by dye (for example, the adhesive may be applied to the periphery of layer 66). If a solid dye is used, then after the pocket 20 is applied to the user's skin and the dye is moistened (the dye can be moistened before application of pocket 20 to the skin but preferably will be moistened after application of the pocket 20 to the skin) the solid dye will be absorbed into or onto the user's skin in the form of the letter "Z".

In order to initially create a desired pattern of dry dye on the under surface of layer 66, many different methods may be employed. One method when using a powder dry dye, for example, involves applying an adhesive suitable for adhering the powder dye to the under surface of layer 66. The adhesive is first applied to the under surface of layer 66 in the form of the desired pattern. The dye powder is then spread over the under surface of layer 66. The dye will then only adhere to the under surface of layer 66 in the form of the desired pattern.

As another example for creating a pattern of dye within a pocket, a gel could be used which, in one form, is non-dying, but which can be combined with a dye so that the gel, in addition to the dye, acts as a dye. The gel will be of a type which is either unaffected by the heat and moisture of the user's skin or which, upon exposure to the heat and moisture of the user's skin, will liquify to a degree to be easily absorbed into the skin while maintaining the desired pattern.

As an example of the use of a gel dye, the entire under surface of layer 66 could be coated with a non-dying gel and then a dye could be imbedded into or onto the surface of the gel in a desired pattern. Alternatively, the under surface of layer 66 could be adhered with a gel dye in a desired pattern. The remaining area(s) of the under surface of layer 66 could then be coated with a non-dying gel. In either case, when the peel away layer is peeled away, and the under surface of layer 66 is adhered to the user's skin, gel from the entire under surface of layer 66 will penetrate the user's skin. However, only those portions of gel containing dye will create a tattoo. As described in greater detail below, different colours of dye may be applied to different portions of the under surface of layer 66 to create a multi-coloured tattoo.

Of course, the more the gel dye behaves as a liquid (as opposed to a solid), the better suited it will be for use in the devices and methods described with respect to liquid dye. The more the gel dye behaves as a solid, the better suited it will be for use in the other devices and methods.

Another embodiment of the invention incorporates a screen or silkscreen printing-type device or process. It is likely that the screen devices described below are better suited than the stencil tattoo pockets described above to produce complex designs or designs with fine features, such as, for example, concentric circles (which may be difficult to create using a stencil tattoo pocket). As well, the screen devices may be helpful to prevent bleeding of the dye (ie: to prevent the dye from seeping beyond the desired outline of the tattoo design). There are many possible variations of the screen device, of which, a few are described below.

Figure 2A:
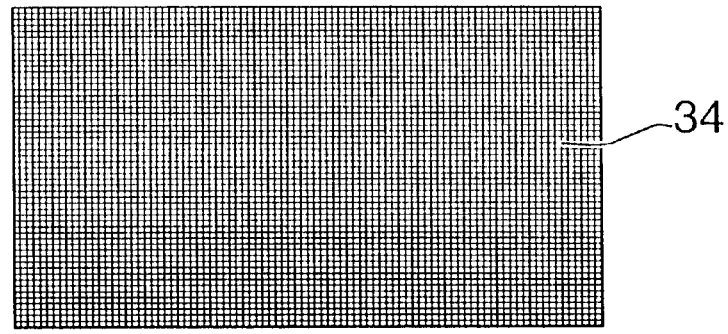
FIG. 2a is a top view of a screen layer.
Figure 2B:
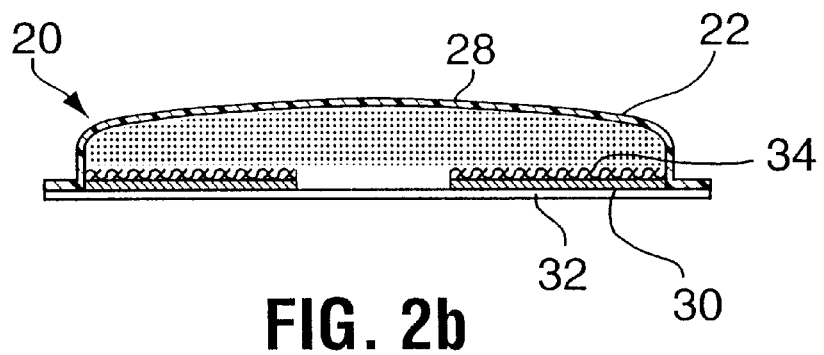
FIG. 2b is a cross-sectional view of a tattoo pocket similar to the embodiment shown in FIG. 1c with a screen layer used instead of a stencil layer.

To the embodiment shown in FIGS. 1a–1c, a screen layer 34, an example of which is shown in top view in FIG. 2a, may be added. Suitable materials for the screen layer include sheet form elastomers and lycra. The screen layer 34 may (i) be added between the dye 28 and the inner layer 24; (ii) completely replace inner layer 24 as shown in the cross-section of pocket 20 in FIG. 2b; or (iii) be added between the inner layer 24 and the peel-away layer 32. For the sake of convenience and simplicity, only alternative (ii) will be considered in the following examples.

Figure 2C:
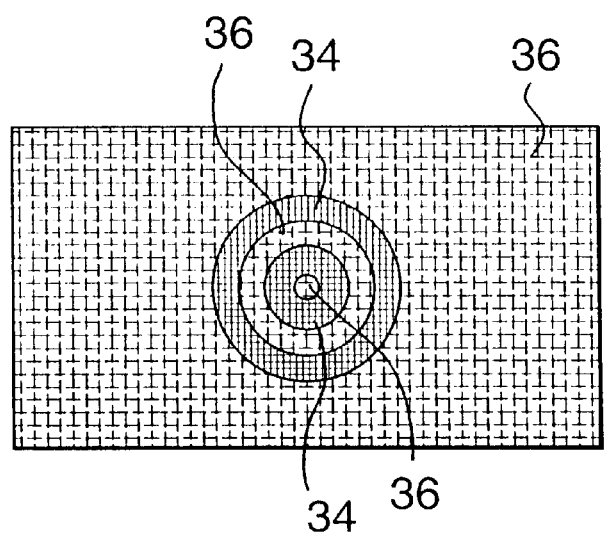
FIG. 2c is a top view of a screen layer with a dye-impermeable coating applied to produce a pattern.

FIG. 2c is a top view of the screen layer 34 in which a dye-impermeable coating (such as a resin-based ink) 36 has been applied to produce a desired pattern. In this case, a bull's eye pattern will be produced. As well, if the adhesive 30 is itself non-permeable to the dye, then the adhesive can be used as impermeable section 36.

As noted above, there are many possible methods by which a pattern may be applied to a screen layer 34. The preferred methods allow for the creation of either a single pattern on a single screen layer 34 (for the creation of a single pocket 20) or for the possible mass production of screens bearing a particular pattern (for the creation of many pockets which will produce the same tattoo). One such method is by silkscreen printing. Another method is by lithography. Yet another method is by a computer printing technique, using, for example, a Condor 1 printer from the company Data Metrix. As an example of the computer printing technique, the user draws a desired tattoo pattern on a computer screen. Then, an appropriately sized piece of dye-permeable fabric is run through the printer, which prints resin-based ink (which is dye-impermeable) onto the fabric in the form of the pattern on the computer screen.

Using the above-noted concepts, pockets can also be used to create multi-colour tattoos (one example was described above). Likely the simplest method for producing multi-colour tattoos is by using solid or gel dyes. One method is described with reference to FIG. 1g which is a bottom view of the dye 28 adhered to, embedded in or partitioned in the under side of layer 66, in the shape of a letter "Z". In this example, the top portion of the "Z" can be one colour dye. The diagonal portion of the "Z" can be another colour dye. The remaining portion of the "Z" can be a third colour dye. To avoid undesired blending of the colours, strips of dye-impermeable material 68 can be adhered to, embedded in or partitioned in material 66 to separate the different colours. Alternatively, non-dying (ie, colourless) gel may be used to separate different colours of dye instead of using the strips of dye-impermeable material 68.

More sophisticated methods can be used to create multi-colour tattoos of greater complexity. For example, a dye of one colour could first be applied to the underside of layer 66 in a desired pattern. Then, a second colour dye could be added in a further desired pattern. For example, if the first colour dye is blue and the second colour dye is yellow, then where the two dyes are added one on top of the other, the resulting colour is green; whereas, where the dyes are not combined, the colour will be either yellow or blue. By combining primary (or other colours) in appropriate combinations, one could create tattoos having different portions of different colours. This method requires that gels of different colours combine to produce the desired resulting colour. The method described below does not require that the different gels actually combine to produce different colours.

Instead of actually combining different colours of dye, a similar effect can be produced by placing one colour dye adjacent another colour dye, similar to what is known in the printing industry as a three or four colour printing process. For example, if small points of blue dye surround small points of yellow dye, then the impression perceived by a viewer may be of a portion of green dye (depending, of course, upon the fineness of the points, the proximity of one dye to another and the distance of the viewer to the tattoo). In other words, even though the dyes have not actually been combined to produce the colour green, the result appears to be green. Alternatively, the dyes may actually combine at their edges to produce the colour of the combination. Either solid or gel dyes can be employed to create multi-colour tattoos according to this embodiment.

Figure 3B:
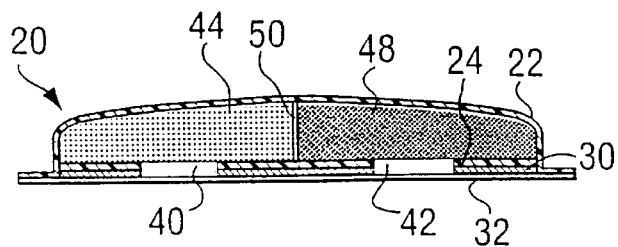
FIG. 3b is a cross-sectional view of a tattoo pocket in accordance with another embodiment of the present invention, allowing the use of multiple colours of dye.

Many other methods can be used to create multi-colour tattoos, regardless of the type of dye. For example, different colours of dye can be isolated within a pocket by barriers which are impermeable to the dye. In one embodiment, as shown in FIG. 3b, which is a cross-sectional view of a pocket 20 for producing a tattoo with two different colours, a barrier 50 is placed between two different colours of dye 44, 48, with the result that the pocket, in this example, will produce a tattoo incorporating one oval of the colour of dye 44 (produced through pattern 40) and another oval of the colour of dye 48 (produced through pattern 42). Of course, the barrier 50 must completely isolate one colour dye from the other. The barrier must be impermeable to the adjacent dyes, and would be adhered, in this embodiment, to both the backing layer 22 and the inner layer 24.

The above-noted embodiments could be manufactured and sold as individual pockets. Alternatively, individual consumers may create their own pockets. One method to produce a customized temporary tattoo may be described as follows. In the preferred embodiment, the user would begin with a combination comprised of impermeable layer 24 of desired dimensions, adhesive layer 30 and peel-away layer 32, as shown in cross-section in FIG. 4b. Of course, the user could also obtain these elements separately, cut or otherwise modify them to the appropriate dimensions and combine them.

Figure 4A:
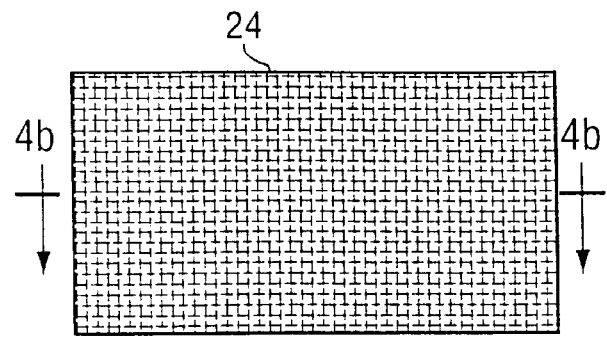
FIG. 4a is a top view of an inner layer, with no pattern removed therefrom.
Figure 3A:
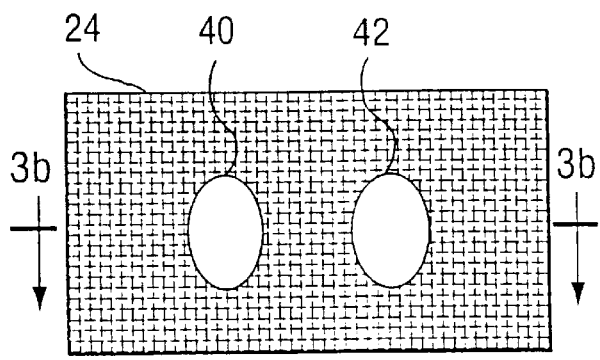
FIG. 3a is a top view of an inner layer, with two patterns removed therefrom.
Figure 4B:
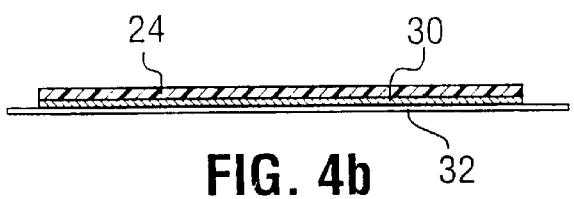
Figure 4C:
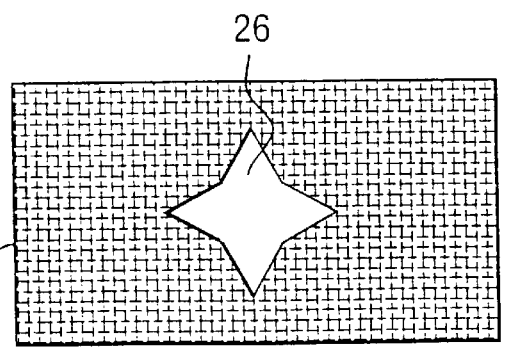
FIG. 4c is a top view of the inner layer of FIG. 4a, with a pattern removed therefrom.

The user then cuts a desired pattern into the inner layer 24 (and also through the peel away layer 32) using a blade or other cutting tool. FIG. 4a illustrates a top view of an uncut inner layer 24 and FIG. 4c illustrates an example of a top view of inner layer 24 in which a pattern 26 has been cut out and removed.

The peel-away layer 24 is then removed and the inner layer 24 is adhered to the desired location of the user's body. An appropriate dye (not shown) is then carefully applied to cover the entire surface area of pattern 26. A backing layer (not shown) is then adhered, by one of any number of methods, to the upper surface of inner layer 24. In one embodiment, after the dye has been applied over pattern 26, an appropriate adhesive is applied to the perimeter of the upper surface of the inner layer 24 and then the perimeter of one side of the backing layer is pressed against the perimeter of the upper surface of the inner layer 24 to adhere the backing layer to the inner layer 24, thereby containing the dye. The adhesive around the perimeter of the upper surface of the inner layer 24 may be pre-applied and protected by a peel-away strip (not shown), for example. When the backing layer is to be applied, the peel-away strip is removed, revealing a clean adhesive which can then adhere the upper perimeter of the upper surface of the inner layer 24 to the backing layer.

Figure 4D:
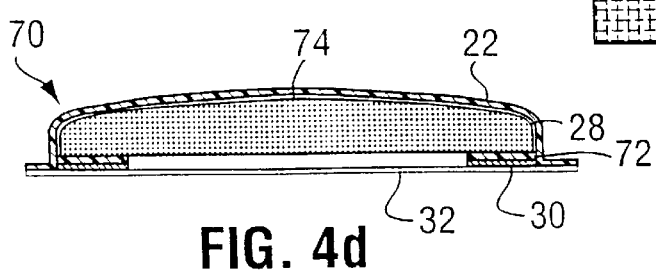
FIG. 4d is a cross-sectional view of a dye pocket according to another embodiment of the invention.

A further modification of the above method reduces the likelihood of the dye 30 leaking or spilling. As above, an inner layer 24 having a desired pattern 26 is adhered to the user's skin. Then, instead of the user applying dye directly over inner layer 24 with the risk of the dye leaking over the edges of inner layer 24, a dye pocket 70, shown in FIG. 4d in cross-section, is used. Dye pocket 70 preferably has the same length and width dimensions as inner layer 24, and is, initially, a self-contained unit, distinct from inner layer 24. Dye pocket 70 is similar to pocket 20 shown in FIG 1a except that whereas layer 24 in pocket 20 defines a tattoo pattern, the comparable layer in pocket 70, dye impermeable layer 72, does not define a tattoo pattern. Rather, dye-impermeable layer 72 either provides an opening 74 or a dye-permeable portion (not shown) through which the dye can flow out. To use dye pocket 70, the inner layer 24, as shown in FIG. 4c, is applied to the user's skin. Peel-away layer 32 is then removed from pocket 70. Then, dye pocket 70 is adhered onto inner layer 24, preferably wither using one of the adhesive methods described in the previous paragraph or by having an adhesive layer 30 revealed on the under surface of impermeable layer 72 when the peel-away layer 32 has been peeled away. The dye 28 then flows out of opening 74 onto inner layer 24 to produce a tattoo in the shape of pattern 26.

Numerous modifications and variations of the present invention are possible in light of the above teachings. It is therefore to be understood that within the scope of the appended claims, the invention may be practised otherwise than as specifically described herein.

What I claim as my invention is:

1. A device for applying a temporary tattoo, the device comprising a pocket containing a dye, the pocket being defined by a removable bottom layer and a backing layer which are impermeable to the dye, the pocket having an inner layer interposed between the dye and the removable layer, the inner layer having a predetermined pattern defined by dye-impermeable and dye-permeable portions.

2. The device of claim 1, wherein the removable layer is initially adhered to the inner layer by an adhesive, which adhesive, once the removable layer has been removed from the inner layer, is capable of securely adhering the inner layer to a user's skin.

3. The device of claim 1, wherein the dye is a non-toxic, long-lasting skin dye.

4. The device of claim 3, wherein the dye is henna or indigo.

5. The device of claim 1, wherein the inner layer is adhered near its perimeter to the backing layer, thereby preventing any leakage of dye between the perimeter of the inner layer and the backing layer.

6. The device of claim 1, wherein the inner layer comprises a thin, dye-impermeable layer, conformable to a user's skin, in which a pattern has been cut out and removed.

7. The device of claim 6, wherein the inner layer further comprises a screen layer, which is permeable to the dye, wherein the screen layer is partially coated, in a desired pattern, with material impermeable to the dye.

8. The device of claim 1, wherein the inner layer comprises a screen layer, permeable to the dye and partially coated, in a desired pattern, with material impermeable to the dye.

9. A device for applying a temporary tattoo which penetrates a user's skin, the device comprising a pocket containing a dye, the pocket being defined by a removable bottom layer and a backing layer which are impermeable to the dye, the dye being interposed between the backing layer and the bottom layer and the dye being in a pre-determined pattern.

10. The device of claim 9 wherein the dye is adhered to the lower surface of the backing layer.

11. The device of claim 9 wherein the dye is one of a gel dye and a solid dye.

12. The device of claim 11 wherein the dye is a solid dye and the backing layer further comprises a moistening portion through which a dye moistening agent can be added.

13. The device of claim 12 wherein the device further comprises a dye-impermeable cover, the cover being also impermeable to the moistening agent wherein the cover is securely adherable over the moistening portion.

14. A method for applying a temporary tattoo using a dye, the method comprising the following steps: creating a pattern in a layer of material, the layer of material including a first surface and a second surface, the first surface comprising a first adhesive covered by a first peel-away layer, the pattern being defined by dye-permeable and dye-impermeable portions; securely adhering the second surface of the layer of material onto a user's skin; applying the dye over the layer of material; removing the first peel-away layer, thereby exposing the first adhesive and securely adhering a dye-impermeable backing layer to the first surface of the layer of material by pressing the backing layer against the first adhesive whereby no dye can leak between the backing layer and the layer of material.

15. The method of claim 14 wherein the layer of material further comprises a peel-away layer, which peel-away layer is initially adhered to the layer of material by an adhesive, which adhesive, once the peel-away layer has been removed from the layer of material, securely adheres the layer of material to the user's skin.

16. The method of claim 14, wherein the dye is a non-toxic long-lasting skin dye.

17. The method of claim 16, wherein the dye is henna or indigo.

18. The method of claim 14, wherein the layer of material comprises a thin, dye-impermeable layer, conformable to a user's skin, wherein creating a pattern comprises cutting out and removing a portion from the layer of material.

19. The method of claim 18, wherein the layer of material further comprises a screen layer, which is permeable to the dye, wherein creating a pattern further comprises coating the screen layer, in a desired pattern, with material impermeable to the dye.

20. A method for applying a temporary tattoo using a dye, the method comprising the following steps: creating a pattern in a layer of material, the pattern being defined by dye-permeable and dye-impermeable portions; securely adhering the layer of material onto a user's skin; applying the dye over the layer of material; securely adhering a dye-impermeable backing layer to the layer of material whereby no dye can leak between the backing layer and the layer of material wherein the layer of material comprises a screen layer, generally permeable to the dye, and wherein creating a pattern comprises coating the screen layer, to define a desired pattern, with material impermeable to the dye.

21. The method of claim 20 wherein coating the screen layer, to define a desired pattern, with material impermeable to the dye comprises the steps of:

selecting the pattern on a computer system, and running the screen layer through a printer driven by the computer system, wherein the printer prints dye-impermeable material onto the screen layer in a form which defines the pattern.

22. A kit for producing a temporary tattoo using a dye, the kit comprising:

(a) a layer of material patternable by the user to yield a pattern defined by dye-permeable and dye-impermeable portions, the layer of material comprising adhesive for adhering the layer of material to a user's skin; and (b) a pocket containing the dye, the pocket being defined by a removable first layer and a second layer which are impermeable to the dye, the pocket comprising adhesive for adhering the pocket to the layer of material after the removable layer is removed.

23. The kit of claim 22 wherein the pocket further comprises a interposed, dye permeable layer, interposed between the dye and the removable layer, the interposed layer being adhered along its perimeter to the backing layer.

24. The kit of claim 23 wherein the removable layer is initially adhered to the interposed layer by the adhesive for adhering the pocket to the layer of material, which adhesive, once the removable layer has been removed from the interposed layer, is capable of securely adhering the passage layer to the layer of material.

25. The kit of claim 22 wherein the dye is a non-toxic, long-lasting skin dye.

26. The kit of claim 25, wherein the dye is henna or indigo.

27. The kit of claim 22, wherein the layer of material comprises a thin, dye-impermeable layer, conformable to a user's skin, in which a pattern has been cut out and removed.

28. The kit of claim 27, wherein the layer of material further comprises a screen layer, which is permeable to the dye, wherein the screen layer is partially coated, to define the desired pattern, with material impermeable to the dye.

29. The kit of claim 22, wherein the layer of material comprises a screen layer, which is permeable to the dye, wherein the screen layer is partially coated, to define the desired pattern, with material impermeable to the dye.

30. The kit of claim 22, wherein the dye is a gel dye.

31. The kit of claim 23, wherein the gel dye comprises the adhesive adhering the pocket to the layer of material.

* * * * *